(12) United States Patent
Lai et al.

(10) Patent No.: US 11,832,791 B2
(45) Date of Patent: Dec. 5, 2023

(54) OPTICAL IMAGING LENS ASSEMBLY AND ENDOSCOPIC OPTICAL DEVICE

(71) Applicant: ALTEK BIOTECHNOLOGY CORPORATION, Hsinchu (TW)

(72) Inventors: Cheng-Yi Lai, Hsinchu (TW); Yang-Chang Chien, Hsinchu (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 47 days.

(21) Appl. No.: 17/477,544

(22) Filed: Sep. 17, 2021

(65) Prior Publication Data

US 2023/0091208 A1    Mar. 23, 2023

(51) Int. Cl.
  *A61B 1/00*     (2006.01)
  *A61B 1/05*     (2006.01)
  *A61B 1/06*     (2006.01)

(52) U.S. Cl.
  CPC .............. *A61B 1/0019* (2013.01); *A61B 1/05* (2013.01); *A61B 1/0661* (2013.01)

(58) Field of Classification Search
  CPC ............ A61B 1/00009; A61B 1/00096; A61B 1/0019; A61B 1/05; A61B 1/051; G02B 9/12
  See application file for complete search history.

(56) References Cited

U.S. PATENT DOCUMENTS

| | | | |
|---|---|---|---|
| 7,027,231 B2 | 4/2006 | Miyano | |
| 11,054,630 B2 | 7/2021 | Uhlendorf et al. | |
| 2008/0204896 A1* | 8/2008 | Shyu | G02B 9/12 359/708 |
| 2011/0228157 A1* | 9/2011 | Tang | G02B 9/12 359/716 |
| 2012/0069432 A1 | 3/2012 | Liang | |
| 2012/0147164 A1* | 6/2012 | Sasamoto | G02B 23/243 359/753 |
| 2012/0212839 A1 | 8/2012 | Hsu | |
| 2017/0235101 A1 | 8/2017 | Huang | |
| 2018/0231747 A1* | 8/2018 | Takada | G02B 1/041 |
| 2021/0030263 A1* | 2/2021 | Kikuchi | A61B 1/043 |
| 2021/0048620 A1* | 2/2021 | Bian | G02B 13/06 |
| 2021/0199920 A1 | 7/2021 | Katakura | |

(Continued)

FOREIGN PATENT DOCUMENTS

| | | |
|---|---|---|
| CN | 103777315 B | 5/2016 |
| CN | 112826421 A | 5/2021 |
| CN | 112925084 A | 6/2021 |

(Continued)

*Primary Examiner* — Aaron B Fairchild
*Assistant Examiner* — Julianna J Nicolaus
(74) *Attorney, Agent, or Firm* — Winston Hsu

(57) ABSTRACT

An optical imaging lens assembly, which is applied for an endoscopic optical device, from an object side to an image side aligned in order includes a first lens element, a second lens element and a third lens element. The first lens element has negative refracting power, and further has a first convex object-side surface and a first image-side surface. The second lens element has positive refracting power, and further has a second convex object-side surface and a second concave image-side surface. The third lens element has positive refracting power, and further has a third convex image-side surface and a third object-side surface.

7 Claims, 7 Drawing Sheets

(56) References Cited

U.S. PATENT DOCUMENTS

2021/0396956 A1* 12/2021 Doujou ................. G02B 13/14

FOREIGN PATENT DOCUMENTS

| CN | 113219638 A | | 8/2021 |
|---|---|---|---|
| JP | 5-107470 A | | 4/1993 |
| JP | 2005308800 A | * | 11/2005 |
| JP | 2017142295 | | 8/2017 |
| KR | 101118910 B1 | * | 3/2012 |
| WO | 2009/063766 A1 | | 5/2009 |

* cited by examiner

OPTICAL IMAGING LENS ASSEMBLY AND ENDOSCOPIC OPTICAL DEVICE

BACKGROUND OF THE INVENTION

1. Field of the Invention

The present invention relates to an optical imaging lens assembly and an endoscopic optical device, and more particularly, to a small-size optical imaging lens assembly with low distortion performance and preferred relative illumination and a related endoscopic optical device.

2. Description of the Prior Art

With the advanced technology, minimally invasive surgery has advantages of small wounds and short recovery time and becomes a trend. The minimally invasive surgery may be performed by using a two-dimensional (2D) or three-dimensional (3D) photography technique. The 2D detection image or the 3D detection image is transmitted onto a screen or a display panel via an endoscopic device for artificial observation. However, the conventional endoscopic device includes complicated lens assembly to capture the detection image; a configuration relation between lenses of the conventional lens assembly must be fixed, so that the conventional endoscopic device cannot achieve diameter miniaturization.

SUMMARY OF THE INVENTION

The present invention provides a small-size optical imaging lens assembly with low distortion performance and preferred relative illumination and a related endoscopic optical device for solving above drawbacks.

According to the claimed invention, an optical imaging lens assembly from an object side to an image side aligned in order includes a first lens element, a second lens element and a third lens element. The first lens element has negative refracting power, and further has a first convex object-side surface and a first image-side surface. The second lens element has positive refracting power, and further has a second convex object-side surface and a second concave image-side surface. The third lens element has positive refracting power, and further has a third convex image-side surface and a third object-side surface.

According to the claimed invention, the first image-side surface is defined as a first concave image-side surface, and the third object-side surface is defined as a third convex object-side surface. The optical imaging lens assembly further includes an aperture stop disposed between the second lens element and the third lens element. A sum of a curvature radius of the first convex object-side surface and a curvature radius of the first image-side surface falls within 3~3.2 mm. A refractive index of each of the first lens element, the second lens element and the third lens element falls within 1.5~1.7, and a sum of the refractive indices of the first lens element, the second lens element and the third lens element falls within 4.7~4.8. A field of view of the optical imaging lens assembly falls within is ranged between 110~145 degrees. A ratio of an effective focal length of the optical imaging lens assembly to a second focal length of the second lens element falls within 0.65~0.75, and a ratio of the effective focal length to a third focal length of the third lens element falls within 0.65~0.75.

According to the claimed invention, an endoscopic optical device includes an optical imaging lens assembly, a light source and an optical sensor. The optical imaging lens assembly from an object side to an image side aligned in order includes a first lens element, a second lens element and a third lens element. The first lens element has negative refracting power, and further has a first convex object-side surface and a first image-side surface. The second lens element has positive refracting power, and further has a second convex object-side surface and a second concave image-side surface. The third lens element has positive refracting power, and further has a third convex image-side surface and a third object-side surface. The light source is adapted to emit an imaging beam toward the optical imaging lens assembly. The optical sensor is adapted to receive a detection image generated by the optical imaging lens assembly.

According to the claimed invention, another endoscopic optical device includes an optical imaging lens assembly, a light source, an optical sensor, a memory, a display interface and an operation processor. The optical imaging lens assembly from an object side to an image side aligned in order includes a first lens element, a second lens element and a third lens element. The first lens element has negative refracting power, and further has a first convex object-side surface and a first image-side surface. The second lens element has positive refracting power, and further has a second convex object-side surface and a second concave image-side surface. The third lens element has positive refracting power, and further has a third convex image-side surface and a third object-side surface. The light source is adapted to emit an imaging beam toward the optical imaging lens assembly. The optical sensor is adapted to receive a detection image generated by the optical imaging lens assembly. The memory is adapted to store the detection image. The operation processor is adapted to analyze the detection image and display an analysis result on the display interface.

The optical imaging lens assembly of the present invention can include the first lens element with the negative refracting power for collecting beams, and the incident beams with large angle can be collected into the optical system due to the negative refracting power, so as to achieve advantages of a wide angle of view, low distortion and preferred relative illumination via the small size lenses; the second lens element can have the positive refracting power for focusing the beams, increasing the angle of view, and providing the low distortion via cooperation with the first lens element, so that the first lens element can be reduced to minimize volume of the optical system; the third lens element can have the positive refracting power, and can be cooperated with the second lens element to focus the beams, and calibrate a light transmission angle incident toward the image plane for enlargement of the relative illumination. When the object-side surface and the image-side surface of the first lens element respectively are convex and concave, the object-side surface and the image-side surface of the second lens element respectively are convex and concave, and the object-side surface and the image-side surface of the third lens element respectively are convex, the distortion aberration and spherical aberration can be effectively corrected to make the optical imaging lens assembly and the related endoscopic optical device have preferred optical performance.

These and other objectives of the present invention will no doubt become obvious to those of ordinary skill in the art after reading the following detailed description of the preferred embodiment that is illustrated in the various figures and drawings.

DETAILED DESCRIPTION

The terms "concave" and "convex" used in the specification and claims should be interpreted based on the definition listed in the specification by the principle of lexicographer. In the present disclosure, the optical system may include at least one lens element to receive imaging beams that are incident on the optical system over a set of angles ranging from parallel to an optical axis to a half field of view (HFOV) angle with respect to the optical axis. The imaging beams pass through the optical system to produce an image on an image plane. The term "a lens element having positive refracting power (or negative refracting power)" means that the paraxial refracting power of the lens element in Gaussian optics is positive (or negative). The term "an object-side (or image-side) surface of a lens element" refers to a specific region of that surface of the lens element at which imaging beams can pass through that specific region. The shape of a region is convex if the imaging beam being parallel to the optical axis and passing through the region is bent toward the optical axis such that the imaging beam intersects the optical axis on the image side of the lens element. The shape of a region is concave if the extension line of the imaging beam being parallel to the optical axis and passing through the region intersects the optical axis on the object side of the lens element.

Alternatively, there is another way for a person having ordinary skill in the art to determine whether the image-side surface and the object-side surface of the lens element is convex or concave by referring to the sign of "Radius of curvature" (the "R" value), which is the paraxial radius of shape of a lens surface. The R value is commonly used in conventional optical design software such as Zemax and CodeV. The R value usually appears in the lens data sheet in the software. For an object-side surface, a positive R value defines that the object-side surface is convex, and a negative R value defines that the object-side surface is concave. Conversely, for an image-side surface, a positive R value defines that the image-side surface is concave, and a negative R value defines that the image-side surface is convex. The result found by using this method should be consistent with the method utilizing intersection of the optical axis by beams or extension lines mentioned above, which determines surface shape by referring to whether the focal point of the collimated beam being parallel to the optical axis is on the object-side or the image-side of the lens element.

Figure 1:
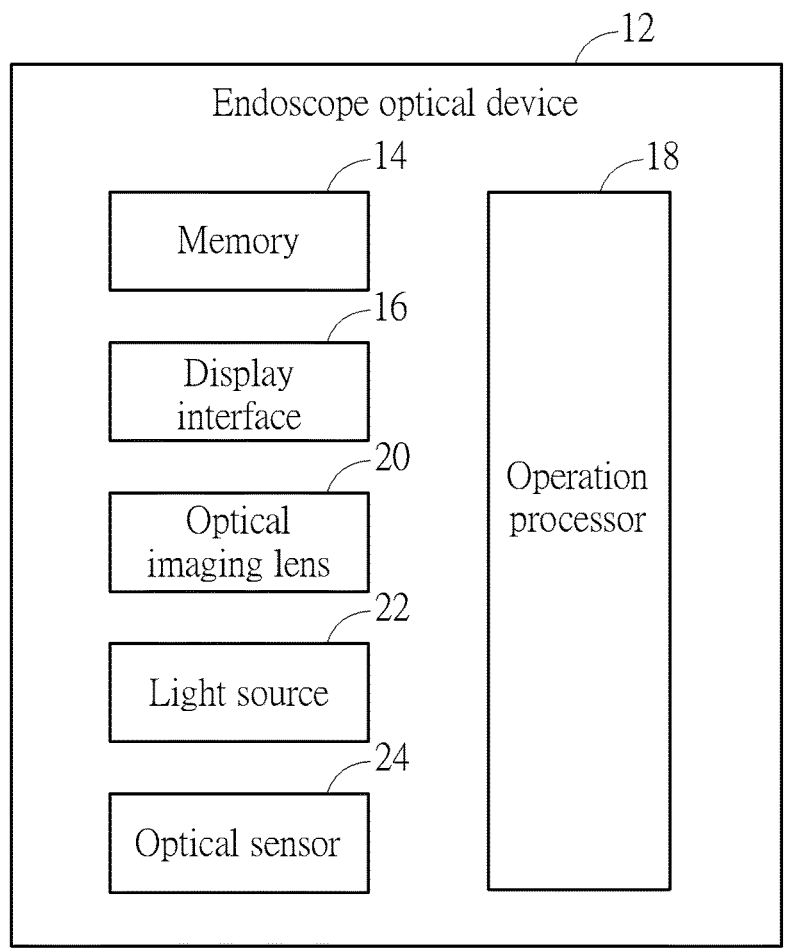
FIG. 1 is a functional block diagram of an endoscopic optical device according to an embodiment of the present invention.

Please refer to FIG. 1. FIG. 1 is a functional block diagram of an endoscopic optical device 12 according to an embodiment of the present invention. The endoscopic optical device 12 can include a memory 14, a display interface 16, an operation processor 18, an optical imaging lens assembly 20, a light source 22 and an optical sensor 24; in the first embodiment, the endoscopic optical device 12 may be an integrated medical instrument. The endoscopic optical device 12 may be design of a flexible hose or similar component, which can insert into a human body to capture a detection image for further analysis and determination. The memory 14 can store the detection image captured by the endoscopic optical device 12 and software for analysis of the detection image. The display interface 16 may be the liquid crystal display, the organic light emitting diode display, or the micro light emitting diode display. A dimension and a type of the display interface 16 can depend on an actual demand. The operation processor 18 can be electrically connected to the endoscopic optical device 12, the memory 14 and the display interface 16. The operation processor 18 can actuate or cease the endoscopic optical device 12 to capture the detection image, and analyze the detection image via the software built-in the memory 14, so as to display an analysis result on the display interface 16.

Figure 2:
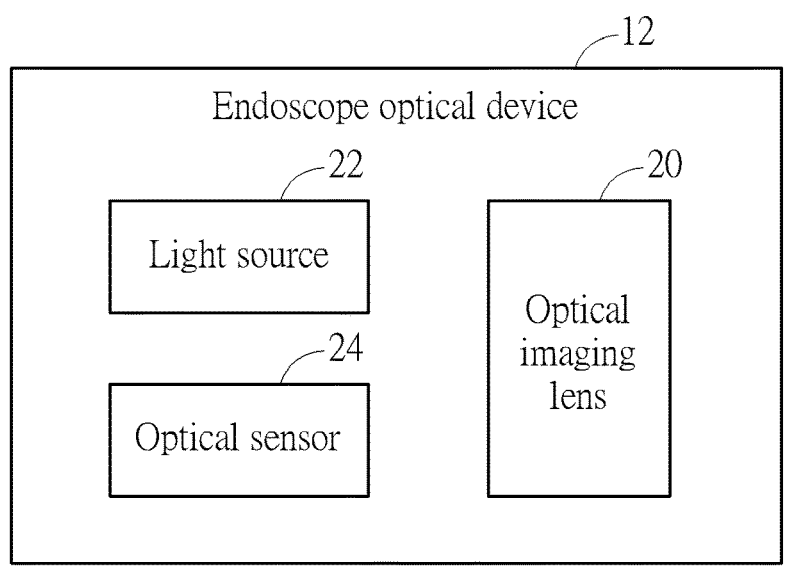
FIG. 2 is a functional block diagram of an endoscopic optical device according to another embodiment of the present invention.

Please refer to FIG. 2. FIG. 2 is a functional block diagram of the endoscopic optical device 12 according to another embodiment of the present invention. In the second embodiment, the endoscopic optical device 12 may be a part of the medical instrument, and be optionally consisted of the optical imaging lens assembly 20, the light source 22 and the optical sensor 24. The optical imaging lens assembly 20 can be formed by several lenses, which are illustrated in following description. The light source 22 can transmit or project an imaging beam toward the optical imaging lens assembly 20 for generation of the detection image. The optical sensor 24 can detect or receive the detection image generated by the optical imaging lens assembly 20. In the present invention, the illumination intensity, the wavelength and the color of the imaging beam emitted by the light source 22 can depend on the actual demand; the dimension and standard of the optical sensor 24 can depend on the actual demand.

The endoscopic optical device 12 of the present invention are image detection product applied for small cavity of the organism, and can have lens assembly with miniaturized dimensions for forming the optical imaging lens assembly 20 with advantages of low distortion and high relative illumination. Detailed structure of the optical imaging lens assembly 20 will be illustrated in the following description.

Figure 3:
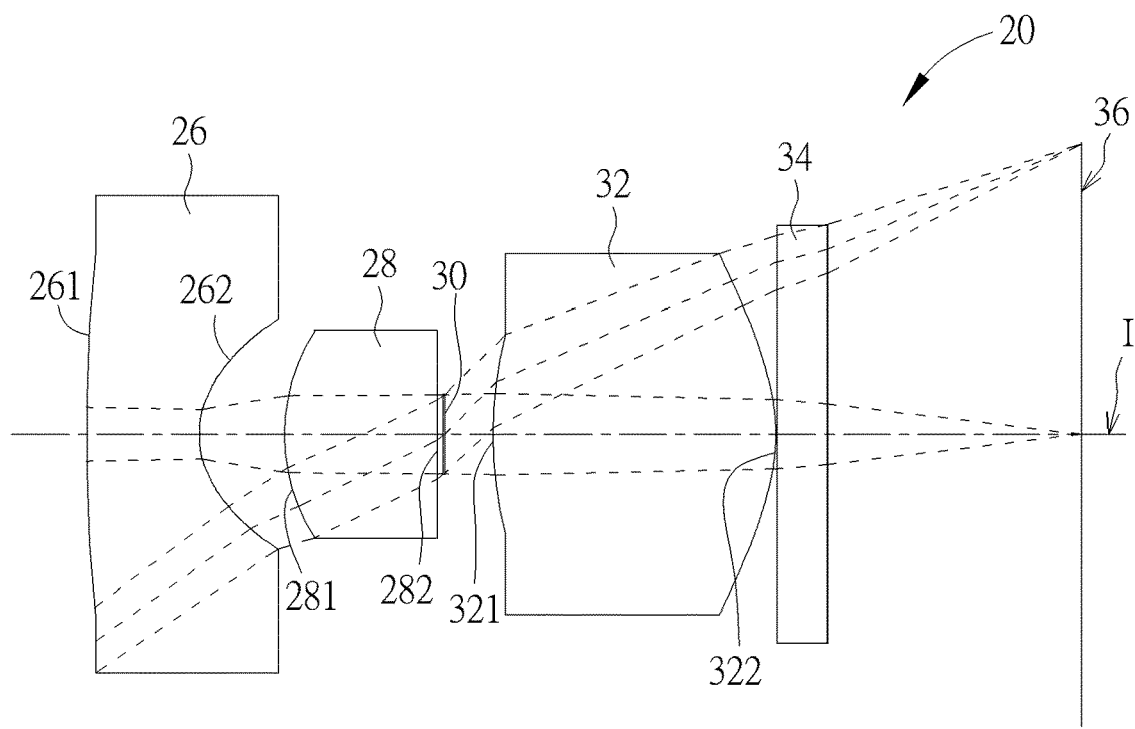
FIG. 3 is a diagram of an optical imaging lens assembly according to a first embodiment of the present invention.

Please refer to FIG. 3. FIG. 3 is a diagram of the optical imaging lens assembly 20 according to a first embodiment of the present invention. The optical imaging lens assembly 20 of three lens elements of the present invention, sequentially located from an object side A1 (where an object is located) to an image side A2 along an optical axis I, includes a first lens element 26, a second lens element 28, an aperture stop 30, a third lens element 32, a filter 34 and an image plane 36. Generally, the first lens element 26, the second lens element 28 and the third lens element 32 may be made of glass material but the present invention is not limited to this, and each of the three lens elements has an appropriate refracting power. In the present invention, optical elements having the refracting power included by the optical imaging lens assembly 20 are the first lens element 26, the second lens element 28 and the third lens element 32. The optical axis I is the optical axis of the entire optical imaging lens assembly 20, and the optical axis of each of the lens elements coincides with the optical axis of the optical imaging lens assembly 20.

Furthermore, the aperture stop 30 of the optical imaging lens assembly 20 can be optionally disposed in an appropriate position. In the embodiment, the aperture stop 30 can be disposed between the second lens element 28 and the third lens element 32. When the beam emitted or reflected by the object (which is not shown in the figures) which is located at the object side A1 enters the optical imaging lens assembly 20 of the present invention, a clear and sharp image can be formed on the image plane 36 at the image side A2 after the beam passing through the first lens element 26, the second lens element 28, the aperture stop 30, the third lens element 32 and the filter 34. In one possible embodiment of the present invention, the filter 34 may be placed between the third lens element 32 and the image plane 36, and it may be a filter of various suitable functions, for example, the filter 34 may be a visible light cut-off filter, for prohibiting the visible light from being transmitted to the image plane 36 to affect the image quality.

Each lens element in the optical imaging lens assembly 20 of the present invention can have an object-side surface facing toward the object side A1 to allow imaging the imaging beam to pass through as well as an image-side surface facing toward the image side A2 to allow the imaging beam to pass through. For example, the first lens element 26 can have an object-side surface 261 and an image-side surface 262; the second lens element 28 can have an object-side surface 281 and an image-side surface 282; the third lens element 32 can have an object-side surface 321 and an image-side surface 322.

The first lens element 26 can have the negative refracting power. The object-side surface 261 of the first lens element 26 can be convex, and the image-side surface 262 of the first lens element 26 can be concave. Besides, both the object-side surface 261 and the image-side surface 262 of the first lens element 26 can be spherical surfaces, but it is not limited thereto. The second lens element 28 can have the positive refracting power. The object-side surface 281 of the second lens element 28 can be convex, and the image-side surface 282 of the second lens element 28 can be concave. Besides, both the object-side surface 281 and the image-side surface 282 of the second lens element 28 can be spherical surfaces, but it is not limited thereto. The third lens element 32 can have the positive refracting power. The object-side surface 321 of the third lens element 32 can be convex, and the image-side surface 322 of the third lens element 32 can be convex. Besides, both the object-side surface 321 and the image-side surface 322 of the third lens element 32 can be spherical surfaces, but it is not limited thereto.

The present invention can define an effective focal length of the optical imaging lens assembly 20 is EFL, and further define HFOV stands for the half field of view which is half of the field of view of the entire optical imaging lens assembly 20. Moreover, the present invention can define a focal length of the first lens element 26 is f1, and a focal length of the second lens element 28 is f2, and a focal length of the third lens element 32 is f3, and a refractive index of the first lens element 26 is n1, and a refractive index of the second lens element 28 is n2, and a refractive index of the third lens element 32 is n3, and an Abbe number of the first lens element 26 is V1, and an Abbe number of the second lens element 28 is V2, and an Abbe number of the third lens element 32 is V3.

Furthermore, the object-side surface 261 of the first lens element 26 has a curvature radius R1, and the image-side surface 262 of the first lens element 26 has a curvature radius R2; a sum of the curvature radius R1 and the curvature radius R2 can fall within 3~3.2, and therefore $3 \leq R1+R2 \leq 3.2$. The refractive index n1 of the first lens element 26, the refractive index n2 of the second lens element 28, and the refractive index n3 of the third lens element 32 can respectively fall within 1.5~1.7; a sum of the refractive indices of the first lens element 26, the second lens element 28 and the third lens element 32 can fall within 4.7~4.8, and thus $4.7 \leq n1+n2+n3 \leq 4.8$. The field of view of the optical imaging lens assembly 20 can fall within 110~145 degrees; the half field of view of tangent function can be valued between 1.43~3.17, which means $1.43 \leq \tan(HFOV) \leq 3.17$. A ratio of the effective focal length EFL of the optical imaging lens assembly 20 relative to the second focal length f2 of the second lens element 28 can fall within 0.6~50.75, and another ratio of the effective focal length EFL relative to the third focal length f3 of the third lens element 32 can fall within 0.65~0.75; therefore, $0.65 \leq f/f2 \leq 0.75$ and $0.65 \leq f/f3 \leq 0.75$.

Figure 4:
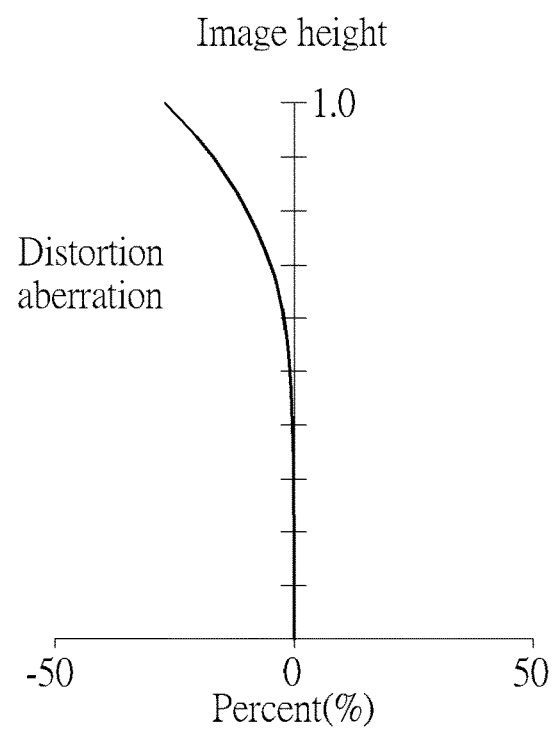
FIG. 4 is a diagram of distortion resulted from the optical imaging lens assembly according to the first embodiment of the present invention.
Figure 5:
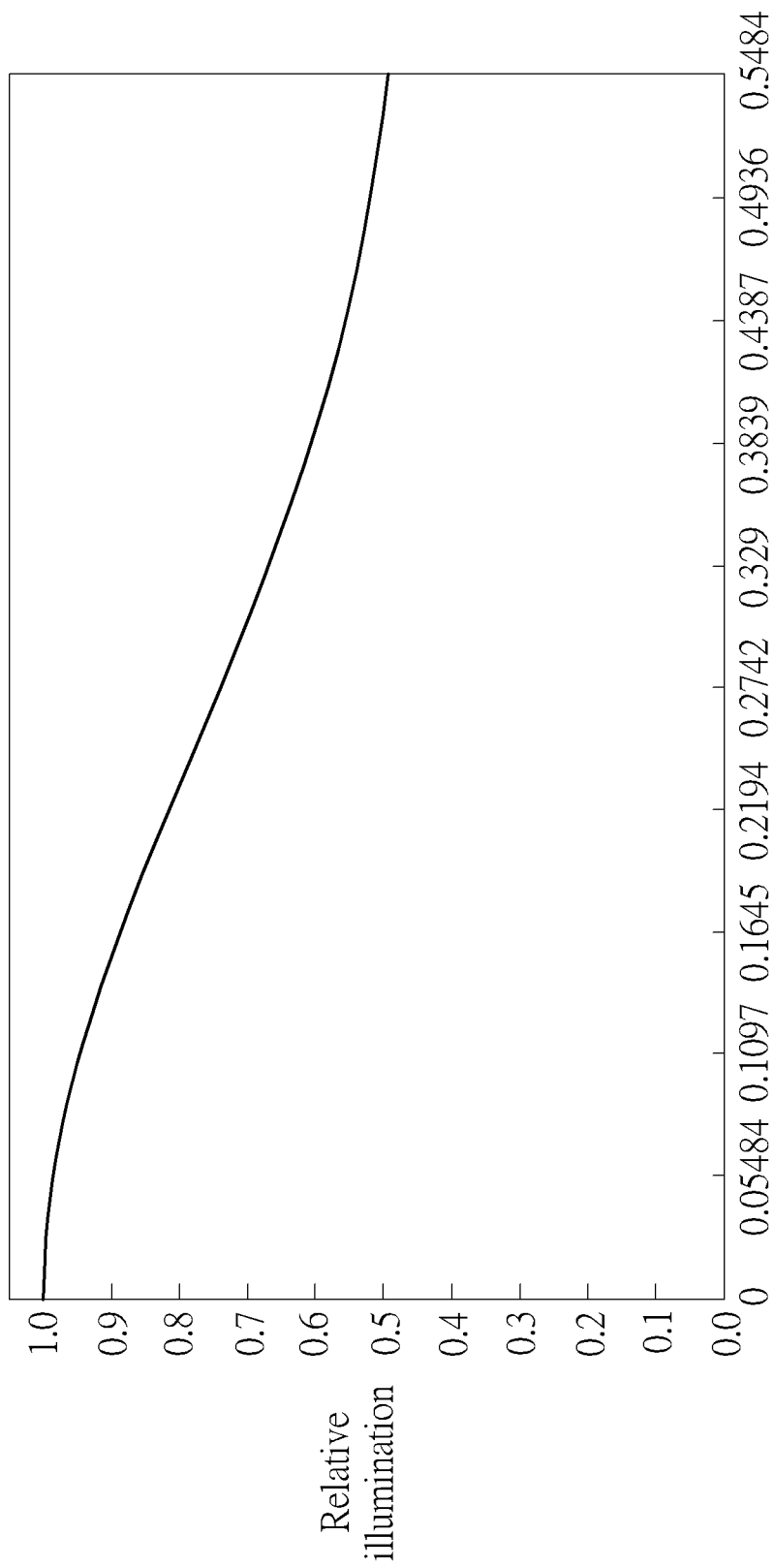
FIG. 5 is a diagram of relative illumination resulted from the optical imaging lens assembly according to the first embodiment of the present invention.

Please refer to FIG. 4 and FIG. 5. FIG. 4 is a diagram of distortion aberration resulted from the optical imaging lens assembly 20 according to the first embodiment of the present invention. FIG. 5 is a diagram of relative illumination resulted from the optical imaging lens assembly 20 according to the first embodiment of the present invention. The optical imaging lens assembly 20 in the first embodiment can have structural and optical parameters illustrated in Table 1, and further have optical data and aspheric surface data respectively illustrated in Table 2 and Table 3. The distortion aberration formed on the image plane 36 can be shown in FIG. 4, and the relative illumination formed on the image plane 36 can be shown in FIG. 5; The Y axis of the distortion aberration in the first embodiment is "image height" for highest point 1.0.

In Table 2, a thickness of the first lens element 26 can be 0.22 mm, and a thickness of the second lens element 28 can be 0.3 mm, and a thickness of the third lens element 32 can be 0.55 mm, and a thickness of the aperture stop 30 can be 0.10 mm, and a thickness of the filter 34 can be 0.10 mm, and an air gap between the first lens element 26 and the second lens element 28 can be 0.17 mm, and an air gap between the second lens element 28 and the aperture stop 30 can be 0.1 mm, and an air gap between the third lens element 32 and the filter 34 can be 0 mm, and an air gap between the filter 34 and the image plane 36 can be 0.5 mm.

TABLE 1

| | |
|---|---|
| EFL | 0.43 |
| f1 | −0.35 |
| f2 | 0.60 |
| f3 | 0.59 |
| HFOV | 60.00 |
| R1 + R2 | 3.13 |

TABLE 1-continued

| | |
|---|---|
| n1 + n2 + n3 | 4.75 |
| tan(HFOV) | 1.73 |
| f/f2 | 0.72 |
| f/f3 | 0.73 |

TABLE 2

| No. | | Curvature radius (mm) | Thickness Air gap Ape. stop distance (mm) | Refractive index | Abbe No. |
|---|---|---|---|---|---|
| | Object | infinite | 0.00 | | |
| 261(26) | First lens element | 2.95 | 0.22 | 1.54(n1) | 55.98(V1) |
| 262(26) | | 0.18 | 0.17 | | |
| 281(28) | Second lens element | 0.36 | 0.30 | 1.66(n2) | 20.40(V2) |
| 282(28) | | 2.70 | 0.01 | | |
| 30 | Aperture stop | infinite | 0.10 | | |
| 321(32) | Third lens element | 0.70 | 0.55 | 1.54(n3) | 55.98(V3) |
| 322(32) | | −0.43 | 0.00 | | |
| 34 | Filter | Infinite | 0.10 | 1.52 | 64.14 |
| | | Infinite | 0.50 | | |
| 36 | Image plane | infinite | | | |

TABLE 3

| No. | 261(26) | 262(26) | 281(28) | 282(28) | 321(32) | 322(32) |
|---|---|---|---|---|---|---|
| K | 0.00 | −1.01 | 0.93 | 0.00 | 0.00 | −0.65 |
| A4 | 0.02 | 8.42 | −2.24 | 2.21 | 8.79 | 1.79 |
| A6 | −6.1 | 0.00 | 1.42 | −26.86 | 0.00 | 16.94 |
| A8 | 0.00 | 0.00 | 0.00 | 0.00 | 0.00 | −34.20 |
| A10 | 0.00 | 0.00 | 0.00 | 0.00 | 0.00 | 0.00 |
| A12 | 0.00 | 0.00 | 0.00 | 0.00 | 0.00 | 0.00 |

Figure 6:
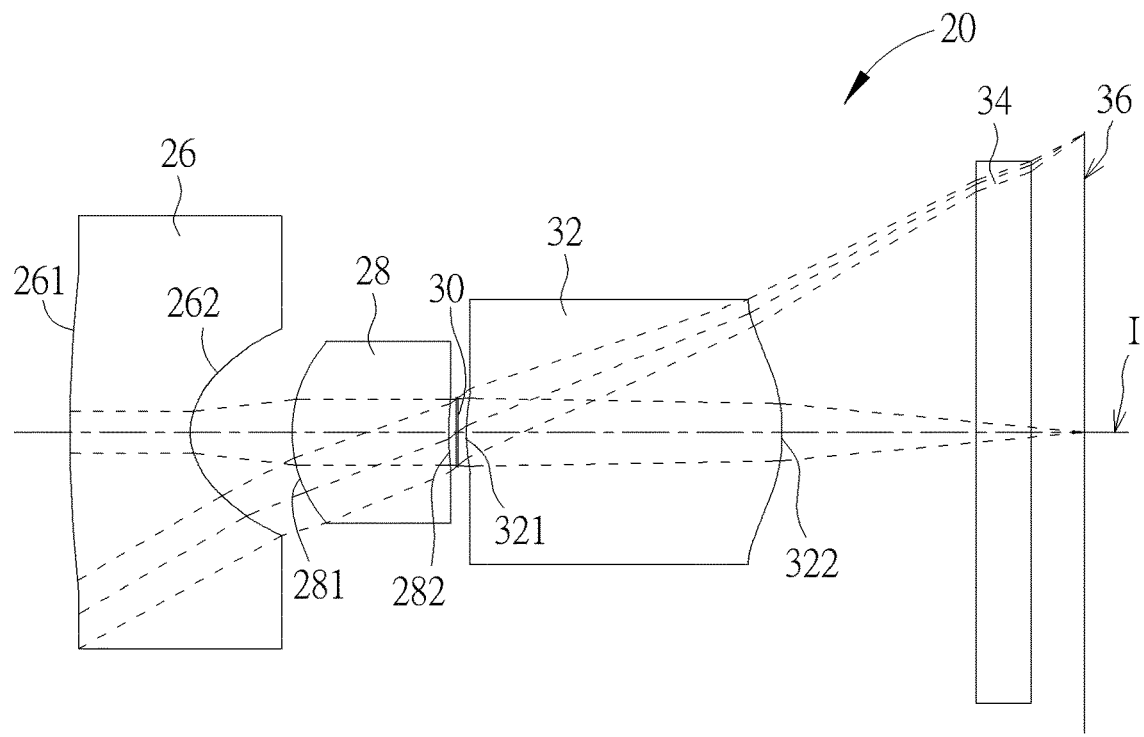
FIG. 6 is a diagram of the optical imaging lens assembly according to a second embodiment of the present invention.
Figure 7:
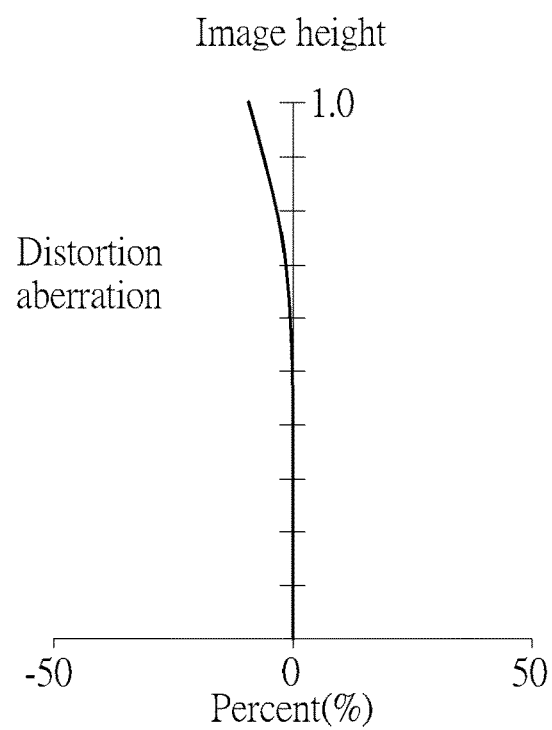
FIG. 7 is a diagram of distortion resulted from the optical imaging lens assembly according to the second embodiment of the present invention.
Figure 8:
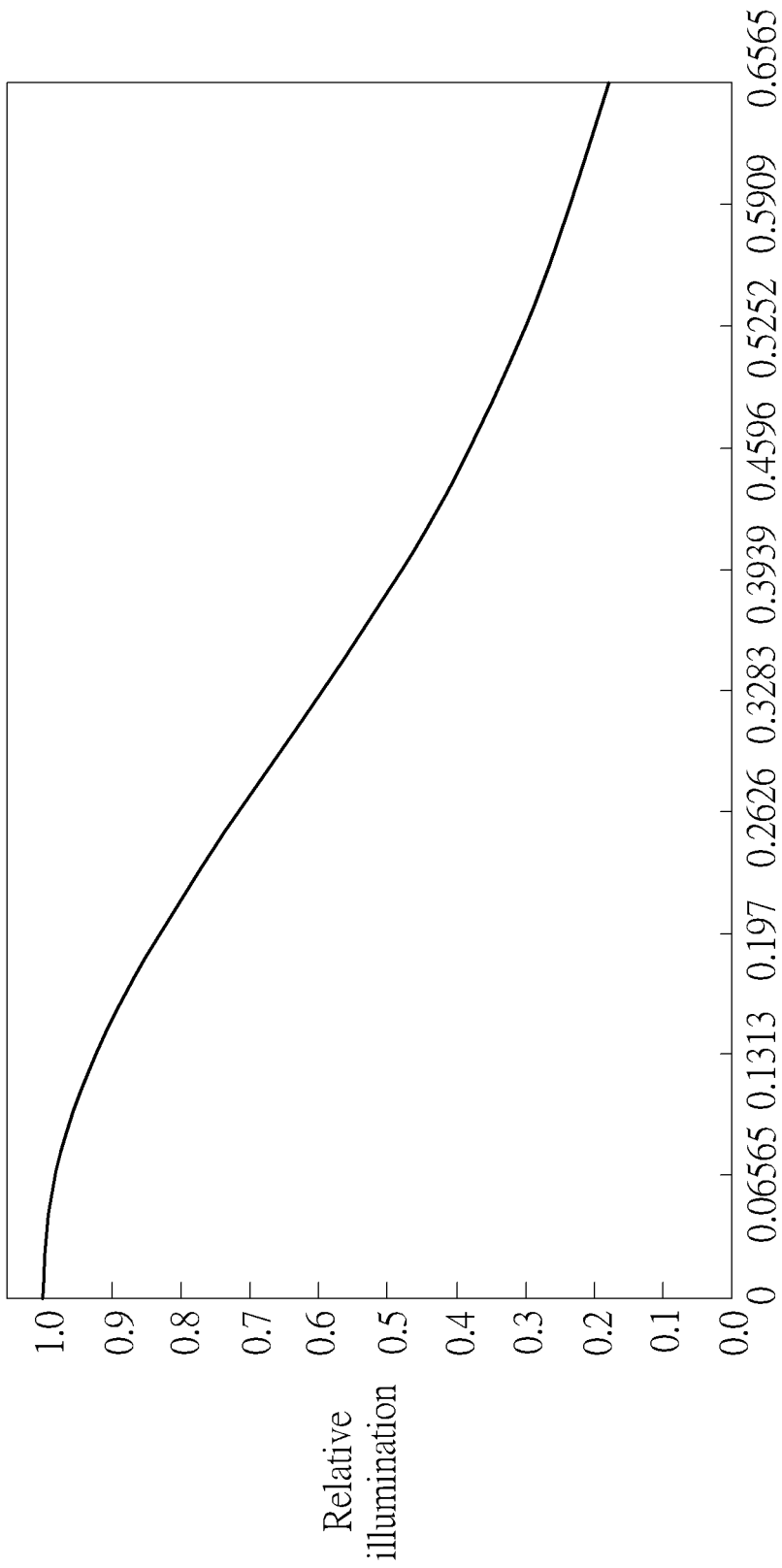
FIG. 8 is a diagram of relative illumination resulted from the optical imaging lens assembly according to the second embodiment of the present invention.

Please refer to FIG. 6 to FIG. 8. FIG. 6 is a diagram of the optical imaging lens assembly 20 according to a second embodiment of the present invention. FIG. 7 is a diagram of distortion aberration resulted from the optical imaging lens assembly 20 according to the second embodiment of the present invention. FIG. 8 is a diagram of relative illumination resulted from the optical imaging lens assembly 20 according to the second embodiment of the present invention. In the second embodiment, elements having the same numerals as one of the first embodiment have similar features and functions, and a detailed description is omitted herein for simplicity. The optical imaging lens assembly 20 in the second embodiment can have structural and optical parameters different from ones of the first embodiment, which are illustrated in Table 4, and further have optical data and aspheric surface data respectively illustrated in Table 5 and Table 6. The distortion aberration formed on the image plane 36 can be shown in FIG. 7, and the relative illumination formed on the image plane 36 can be shown in FIG. 8; The Y axis of the distortion aberration is "image height" for highest point 1.0.

In Table 5, a thickness of the first lens element 26 can be 0.22 mm, and a thickness of the second lens element 28 can be 0.29 mm, and a thickness of the third lens element 32 can be 0.58 mm, and a thickness of the aperture stop 30 can be 0.02 mm, and a thickness of the filter 34 can be 0.10 mm, and an air gap between the first lens element 26 and the second lens element 28 can be 0.19 mm, and an air gap between the second lens element 28 and the aperture stop 30 can be 0.01 mm, and an air gap between the third lens element 32 and the filter 34 can be 0.36 mm, and an air gap between the filter 34 and the image plane 36 can be 0.1 mm.

TABLE 4

| | |
|---|---|
| EFL | 0.43 |
| f1 | −0.34 |
| f2 | 0.60 |
| f3 | 0.60 |
| HFOV | 60.00 |
| R1 + R2 | 3.07 |
| n1 + n2 + n3 | 4.75 |
| tan(HFOV) | 1.73 |
| f/f2 | 0.71 |
| f/f3 | 0.71 |

TABLE 5

| No. | | Curvature radius (mm) | Thickness Air gap Ape. stop distance (mm) | Refractive index | Abbe No. |
|---|---|---|---|---|---|
| | Object | infinite | 0.00 | | |
| 261(26) | First lens element | 2.90 | 0.22 | 1.54(n1) | 55.98(V1) |
| 262(26) | | 0.17 | 0.19 | | |
| 281(28) | Second lens element | 0.36 | 0.29 | 1.66(n2) | 20.40(V2) |
| 282(28) | | 2.70 | 0.01 | | |
| 30 | Aperture stop | infinite | 0.02 | | |
| 321(32) | Third lens element | 0.70 | 0.58 | 1.54(n3) | 55.98(V3) |
| 322(32) | | −0.43 | 0.36 | | |
| 34 | Filter | Infinite | 0.10 | 1.52 | 64.14 |
| | | Infinite | 0.10 | | |
| 36 | Image plane | infinite | | | |

TABLE 6

| No. | 261(26) | 262(26) | 281(28) | 282(28) | 321(32) | 322(32) |
|---|---|---|---|---|---|---|
| K | 0.00 | −0.99 | 0.90 | 0.00 | 0.00 | −0.70 |
| A4 | −0.31 | 4.54 | −3.66 | 10.16 | 13.47 | 1.56 |
| A6 | −4.70 | 0.00 | 95.22 | 0.00 | 0.00 | 53.45 |
| A8 | 0.00 | 0.00 | 0.00 | 0.00 | 0.00 | −32.97 |
| A10 | 0.00 | 0.00 | 1.23 | 0.00 | 0.00 | 0.00 |
| A12 | 0.00 | 0.00 | 0.00 | 0.00 | 0.00 | 0.00 |

Figure 9:
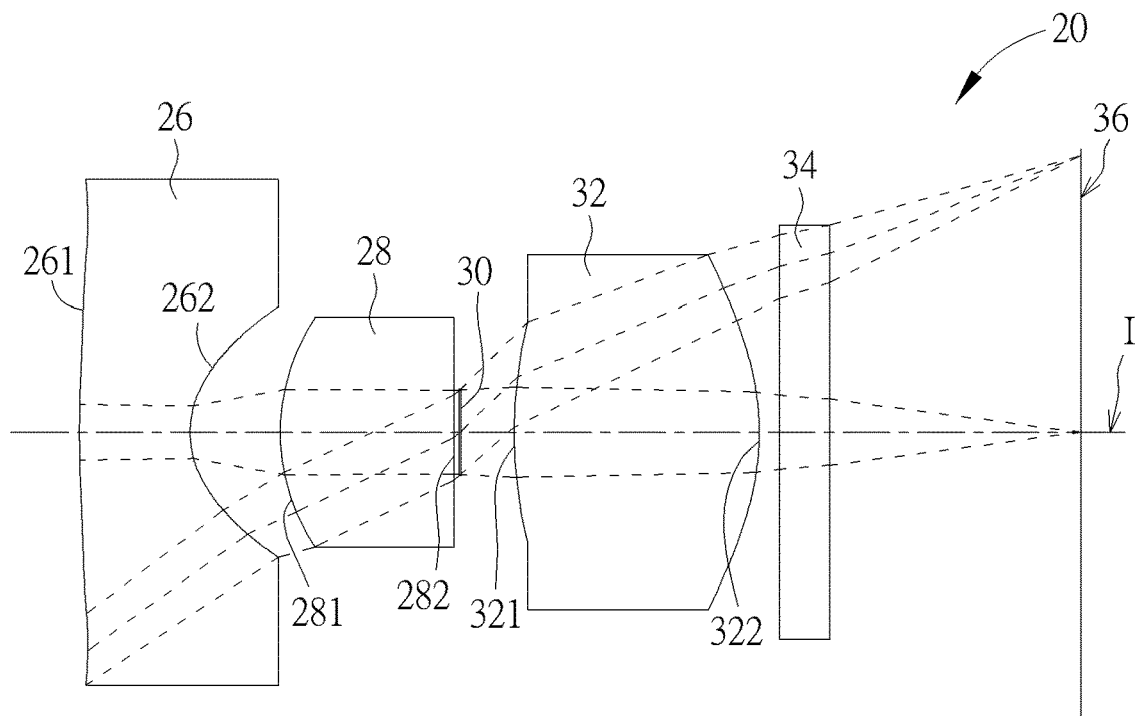
FIG. 9 is a diagram of the optical imaging lens assembly according to a third embodiment of the present invention.
Figure 10:
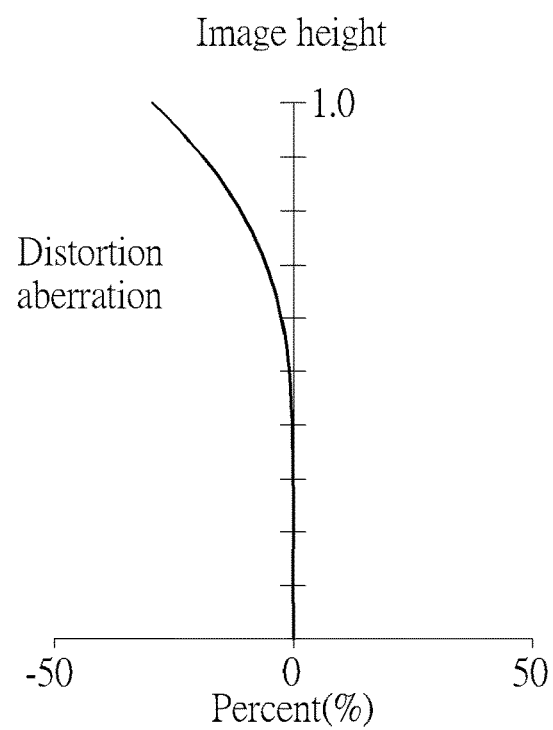
FIG. 10 is a diagram of distortion resulted from the optical imaging lens assembly according to the third embodiment of the present invention.
Figure 11:
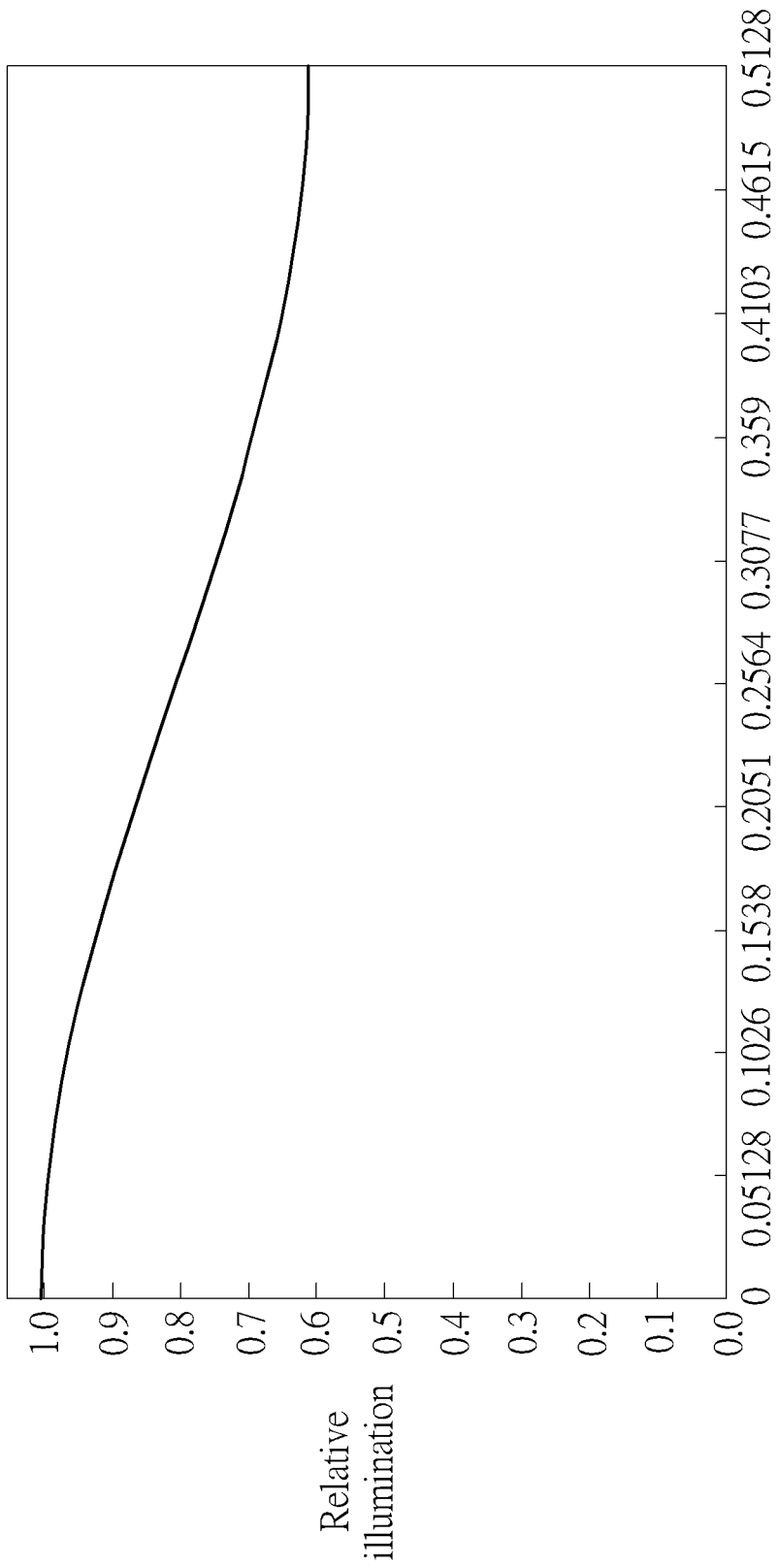
FIG. 11 is a diagram of relative illumination resulted from the optical imaging lens assembly according to the third embodiment of the present invention.

Please refer to FIG. 9 to FIG. 11. FIG. 9 is a diagram of the optical imaging lens assembly 20 according to a third embodiment of the present invention. FIG. 10 is a diagram of distortion aberration resulted from the optical imaging lens assembly 20 according to the third embodiment of the present invention. FIG. 11 is a diagram of relative illumination resulted from the optical imaging lens assembly 20 according to the third embodiment of the present invention. In the third embodiment, elements having the same numerals as one of the above-mentioned embodiments have similar features and functions, and a detailed description is omitted herein for simplicity. The optical imaging lens assembly 20 in the third embodiment can have structural and optical parameters different from ones of the above-mentioned embodiments, which are illustrated in Table 7, and further have optical data and aspheric surface data respectively illustrated in Table 8 and Table 9. The distortion aberration formed on the image plane 36 can be shown in FIG. 10, and the relative illumination formed on the image plane 36 can be shown in FIG. 11; The Y axis of the distortion aberration is "image height" for highest point 1.0.

In Table 8, a thickness of the first lens element 26 can be 0.22 mm, and a thickness of the second lens element 28 can be 0.35 mm, and a thickness of the third lens element 32 can be 0.49 mm, and a thickness of the aperture stop 30 can be 0.11 mm, and a thickness of the filter 34 can be 0.18 mm, and an air gap between the first lens element 26 and the second lens element 28 can be 0.18 mm, and an air gap between the second lens element 28 and the aperture stop 30 can be 0.01 mm, and an air gap between the third lens element 32 and the filter 34 can be 0.04 mm, and an air gap between the filter 34 and the image plane 36 can be 0.5 mm.

TABLE 7

| | |
|---|---|
| EFL | 0.42 |
| f1 | −0.33 |
| f2 | 0.60 |
| f3 | 0.59 |
| HFOV | 60.00 |
| R1 + R2 | 3.17 |
| n1 + n2 + n3 | 4.75 |
| tan(HFOV) | 1.73 |
| f/f2 | 0.70 |
| f/f3 | 0.71 |

TABLE 8

| No. | | Curvature radius (mm) | Thickness Air gap Ape. stop distance (mm) | refractive index | Abbe No. |
|---|---|---|---|---|---|
| | Object | infinite | 0.00 | | |
| 261(26) | First lens element | 3.00 | 0.22 | 1.54(n1) | 55.98(V1) |
| 262(26) | | 0.17 | 0.18 | | |
| 281(28) | Second lens element | 0.36 | 0.35 | 1.66(n2) | 20.40(V2) |
| 282(28) | | 2.27 | 0.01 | | |
| 30 | Aperture stop | infinite | 0.11 | | |
| 321(32) | Third lens element | 0.71 | 0.49 | 1.54(n3) | 55.98(V3) |
| 322(32) | | −0.44 | 0.04 | | |
| 34 | Filter | Infinite | 0.10 | 1.52 | 64.14 |
| | | Infinite | 0.50 | | |
| 36 | Image plane | infinite | | | |

TABLE 9

| No. | 261(26) | 262(26) | 281(28) | 282(28) | 321(32) | 322(32) |
|---|---|---|---|---|---|---|
| K | 0.00 | −1.02 | 0.90 | 0.00 | −26.90 | −0.67 |
| A4 | −0.06 | 8.38 | −2.65 | −0.91 | 8.33 | 1.79 |
| A6 | −6.24 | −60.00 | −20.38 | 178.50 | −162.12 | 14.65 |
| A8 | 0.00 | 0.00 | 0.00 | 0.00 | 0.00 | −51.63 |
| A10 | 0.00 | 0.00 | 0.00 | 0.00 | 0.00 | 0.00 |
| A12 | 0.00 | 0.00 | 0.00 | 0.00 | 0.00 | 0.00 |

In order to ensure the optical quality of the optical imaging lens assembly, and considering the difficulty of manufacturing, the curvature radius, the lens thickness, the air gap, the refractive index and the Abbe number in the embodiments of the present invention can be optionally matched and designed in a changeable manner. The contents in the embodiments of the present invention include but are not limited to the focal length, the thickness of the lens element, the Abbe number, or other optical parameters. When the numerical limit of the optical parameters shown in the above-mentioned embodiments are satisfied, the optical imaging lens assembly of the present invention can have preferred configuration.

The ranges of the aforementioned optical parameters, the aforementioned comparative relations between the optical parameters, and a maximum value, a minimum value, and the numerical range between the maximum value and the minimum value of the aforementioned conditional expressions are all implementable and belong to the scope of the invention. The aforementioned description is for exemplary explanation, but the present invention is not limited thereto. The embodiments of the present invention are all implementable. In addition, a combination of partial features in a same embodiment can be selected, and the combination of partial features includes but is not limited to the surface shape of the lens element, the refracting power, the conditional expression or the like, or a combination thereof. The description of the embodiments is for explaining the specific embodiments of the principles of the invention, but the invention is not limited thereto; that is to say, the embodiments and the drawings are for exemplifying, but the present invention is not limited thereto.

In conclusion, the optical imaging lens assembly of the present invention can include the first lens element with the negative refracting power for collecting beams, and the incident beams with large angle can be collected into the optical system due to the negative refracting power, so as to achieve advantages of the wide angle of view, the low distortion and the preferred relative illumination via the small size lenses; the second lens element can have the positive refracting power for focusing the beams, increasing the angle of view, and providing the low distortion via cooperation with the first lens element, so that the first lens element can be reduced to minimize volume of the optical system; the third lens element can have the positive refracting power, and can be cooperated with the second lens element to focus the beams, and calibrate a light transmission angle incident on the image plane for enlargement of the relative illumination. If the object-side surface and the image-side surface of the first lens element respectively are convex and concave, the object-side surface and the image-side surface of the second lens element respectively are convex and concave, and the object-side surface and the image-side surface of the third lens element respectively are convex, the distortion aberration and spherical aberration can be effectively corrected to make the optical imaging lens assembly and the related endoscopic optical device have preferred optical performance.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An endoscopic optical device, comprising:
   an optical imaging lens assembly comprising:
      a first lens element, a second lens element and a third lens element aligned in order from an object side to an image side;

the first lens element having negative refracting power, and further having a first convex object-side surface and a first image-side surface;

the second lens element having positive refracting power, and further having a second convex object-side surface and a second concave image-side surface;

the third lens element having positive refracting power, and further having a third convex image-side surface and a third object-side surface; and an aperture stop disposed between the second lens element and the third lens element, and a thickness of the aperture stop falling within 0.02 mm~0.11 mm:

a light source adapted to emit an imaging beam toward the optical imaging lens assembly; and an optical sensor adapted to receive a detection image generated by the optical imaging lens assembly;

wherein a sum of a curvature radius of the first convex object-side surface and a curvature radius of the first image-side surface falls within 3~3.2 mm, a refractive index of each of the first lens element, the second lens element and the third lens element falls within 1.5~1.7, and a sum of the refractive indices of the first lens element, the second lens element and the third lens element falls within 4.7~4.8, a field of view of the optical imaging lens assembly falls within 110~145 degrees, and a ratio of an effective focal length of the optical imaging lens assembly to a second focal length of the second lens element falls within 0.65~0.75, and a ratio of the effective focal length to a third focal length of the third lens element falls within 0.650.75.

2. The endoscopic optical device of claim 1, wherein the first image-side surface is defined as a first concave image-side surface, and the third object-side surface is defined as a third convex object-side surface.

3. An endoscopic optical device comprising:

an optical imaging lens assembly comprising:

a first lens element, a second lens element and a third lens element aligned in order from an object side to an image side;

the first lens element having negative refracting power, and further having a first convex object-side surface and a first image-side surface;

the second lens element having positive refracting power, and further having a second convex object-side surface and a second concave image-side surface, a thickness of the second lens element falling within 0.29 mm~0.35 mm;

the third lens element having positive refracting power, and further having a third convex image-side surface and a third object-side surface, a thickness of the third lens element falling within 0.49 mm~0.58 mm; and an aperture stop disposed between the second lens element and the third lens element, and a thickness of the aperture stop falling within 0.02 mm 0.11 mm;

wherein a sum of a curvature radius of the first convex object-side surface and a curvature radius of the first image-side surface falls within 3~3.2 mm;

a light source adapted to emit an imaging beam toward the optical imaging lens assembly; and an optical sensor adapted to receive a detection image generated by the optical imaging lens assembly;

a memory adapted to store the detection image;

a display interface; and an operation processor adapted to analyze the detection image and display an analysis result on the display interface.

4. The endoscopic optical device of claim 3, wherein the first image-side surface is defined as a first concave image-side surface, and the third object-side surface is defined as a third convex object-side surface.

5. The endoscopic optical device of claim 3, wherein a refractive index of each of the first lens element, the second lens element and the third lens element falls within 1.5~1.7, and a sum of the refractive indices of the first lens element, the second lens element and the third lens element falls within 4.7~4.8.

6. The endoscopic optical device of claim 3, wherein a field of view of the optical imaging lens assembly falls within 110~145 degrees.

7. The endoscopic optical device of claim 3, wherein a ratio of an effective focal length of the optical imaging lens assembly to a second focal length of the second lens element falls within 0.65~0.75, and a ratio of the effective focal length to a third focal length of the third lens element falls within 0.65~0.75.

* * * * *